(12) United States Patent
Banet et al.

(10) Patent No.: US 8,449,469 B2
(45) Date of Patent: May 28, 2013

(54) TWO-PART PATCH SENSOR FOR MONITORING VITAL SIGNS

(75) Inventors: Matthew John Banet, Del Mar, CA (US); Zhou Zhou, La Jolla, CA (US); Kenneth Robert Hunt, Vista, CA (US)

(73) Assignee: Sotera Wireless, Inc., San Diego, CA (US)

( * ) Notice: Subject to any disclaimer, the term of this patent is extended or adjusted under 35 U.S.C. 154(b) by 1779 days.

(21) Appl. No.: 11/558,538

(22) Filed: Nov. 10, 2006

(65) Prior Publication Data

US 2008/0114220 A1    May 15, 2008

(51) Int. Cl.
*A61B 5/02* (2006.01)
*A61B 5/04* (2006.01)
*A61B 6/00* (2006.01)
*A61B 8/00* (2006.01)
*A61B 8/14* (2006.01)

(52) U.S. Cl.
USPC ........... 600/483; 600/481; 600/485; 600/513; 600/509; 600/476; 600/479; 600/438; 600/459

(58) Field of Classification Search
USPC ................. 600/481, 483–485, 500–503, 372, 600/382–384, 386, 391, 395–397
See application file for complete search history.

(56) References Cited

U.S. PATENT DOCUMENTS

| | | | |
|---|---|---|---|
| 3,412,729 A | 11/1968 | Smith | |
| 4,063,551 A | 12/1977 | Sweeney | |
| 4,080,966 A | 3/1978 | McNally et al. | |
| 4,094,308 A | 6/1978 | Cormier | |
| 4,245,648 A | 1/1981 | Trimmer et al. | |
| 4,289,141 A | 9/1981 | Cormier | |
| 4,320,767 A | 3/1982 | Villa-Real | |
| 4,367,752 A | 1/1983 | Jimenez et al. | |
| 4,380,240 A | 4/1983 | Jobsis et al. | |
| 4,425,920 A | 1/1984 | Bourland et al. | |
| 4,653,498 A | 3/1987 | New, Jr. et al. | |
| 4,681,118 A | 7/1987 | Asai et al. | |

(Continued)

OTHER PUBLICATIONS

Assessment of Vasoactive Agents and Vascular Aging by the Second Derivative of Photoplethysmogram Waveform, Takazawa et. al, Hypertension 32: 365-370, 1998.

(Continued)

*Primary Examiner* — Navin Natnithithadha
(74) *Attorney, Agent, or Firm* — Michael A. Whittaker; Acuity Law Group, P.C.

(57) ABSTRACT

A two-component monitoring device and system for monitoring blood pressure from a patient is disclosed herein. The two-component monitoring device includes a disposable component and a main component. The disposable component features: i) a backing structure having a first aperture; and ii) first and second electrodes, each electrode connected to the backing structure and including an electrical lead and a conductive electrode material, and configured to generate an electrical signal that passes through the electrical lead when the conductive electrode material contacts the patient. The main component includes: i) first and second connectors configured to connect to the first and second electrical leads to receive the first and second electrical signals; and ii) an optical component comprising a light source that generates optical radiation and a photodetector that detects the optical radiation. The optical component inserts into the first aperture of the disposable component. The main component optionally includes an acoustic sensor. The system utilizes a processing device, connected to the monitoring device by a cable which receives and processes a plurality of signals to determine real-time blood-pressure values for the patient.

3 Claims, 8 Drawing Sheets

U.S. PATENT DOCUMENTS

| | | | |
|---|---|---|---|
| 4,777,954 A | 10/1988 | Kuesch et al. | |
| 4,825,879 A | 5/1989 | Tan et al. | |
| 4,846,189 A | 7/1989 | Sun | |
| 4,869,261 A | 9/1989 | Penaz | |
| 4,917,108 A | 4/1990 | Mault | |
| 4,957,109 A * | 9/1990 | Groeger et al. | 600/391 |
| 5,002,055 A | 3/1991 | Merki et al. | |
| 5,038,792 A | 8/1991 | Mault | |
| 5,054,494 A | 10/1991 | Lazzaro et al. | |
| 5,111,817 A | 5/1992 | Clark et al. | |
| 5,140,990 A | 8/1992 | Jones et al. | |
| 5,178,155 A | 1/1993 | Mault | |
| 5,179,958 A | 1/1993 | Mault | |
| 5,213,099 A | 5/1993 | Tripp, Jr. | |
| 5,237,997 A | 8/1993 | Greubel et al. | |
| 5,309,916 A | 5/1994 | Hatschek | |
| 5,316,008 A | 5/1994 | Suga et al. | |
| 5,368,039 A | 11/1994 | Moses | |
| 5,435,315 A | 7/1995 | McPhee et al. | |
| 5,485,848 A | 1/1996 | Jackson et al. | |
| 5,551,438 A | 9/1996 | Moses | |
| 5,566,671 A * | 10/1996 | Lyons | 600/372 |
| 5,632,272 A | 5/1997 | Diab et al. | |
| 5,727,558 A | 3/1998 | Hakki et al. | |
| 5,743,857 A | 4/1998 | Shinoda et al. | |
| 5,788,634 A | 8/1998 | Suda et al. | |
| 5,836,300 A | 11/1998 | Mault | |
| 5,857,975 A | 1/1999 | Golub | |
| 5,865,755 A | 2/1999 | Golub | |
| 5,865,758 A | 2/1999 | Louzianine | |
| 5,891,042 A | 4/1999 | Sham et al. | |
| 5,921,936 A | 7/1999 | Inukai et al. | |
| 6,004,274 A | 12/1999 | Nolan et al. | |
| 6,013,009 A | 1/2000 | Karkanen | |
| 6,050,940 A | 4/2000 | Braun et al. | |
| 6,176,831 B1 | 1/2001 | Voss et al. | |
| 6,224,548 B1 | 5/2001 | Gopinathan et al. | |
| 6,245,014 B1 | 6/2001 | Brainard, II | |
| 6,272,936 B1 | 8/2001 | Oreper et al. | |
| 6,280,390 B1 | 8/2001 | Akselrod et al. | |
| 6,334,065 B1 | 12/2001 | Al-Ali et al. | |
| 6,336,900 B1 | 1/2002 | Alleckson et al. | |
| 6,364,842 B1 | 4/2002 | Amano et al. | |
| 6,371,921 B1 | 4/2002 | Caro et al. | |
| 6,375,614 B1 | 4/2002 | Braun et al. | |
| 6,385,473 B1 * | 5/2002 | Haines et al. | 600/393 |
| 6,398,727 B1 | 6/2002 | Bui et al. | |
| 6,413,223 B1 | 7/2002 | Yang et al. | |
| 6,416,471 B1 * | 7/2002 | Kumar et al. | 600/300 |
| 6,432,061 B1 | 8/2002 | Nissila et al. | |
| 6,443,905 B1 | 9/2002 | Nissila et al. | |
| 6,443,906 B1 | 9/2002 | Ting et al. | |
| 6,450,953 B1 * | 9/2002 | Place et al. | 600/300 |
| 6,454,708 B1 * | 9/2002 | Ferguson et al. | 600/300 |
| 6,475,146 B1 | 11/2002 | Frelburger et al. | |
| 6,475,153 B1 | 11/2002 | Khair et al. | |
| 6,477,397 B1 | 11/2002 | Ronkainen et al. | |
| 6,494,829 B1 * | 12/2002 | New et al. | 600/300 |
| 6,511,436 B1 | 1/2003 | Asmar | |
| 6,514,211 B1 | 2/2003 | Baura | |
| 6,527,711 B1 | 3/2003 | Stivoric et al. | |
| 6,533,729 B1 | 3/2003 | Khair et al. | |
| 6,546,269 B1 | 4/2003 | Kurnik | |
| 6,553,247 B1 | 4/2003 | Rytky | |
| 6,556,852 B1 | 4/2003 | Schulze et al. | |
| 6,558,321 B1 | 5/2003 | Burd et al. | |
| 6,571,200 B1 | 5/2003 | Mault | |
| 6,595,929 B2 | 7/2003 | Stivoric et al. | |
| 6,599,251 B2 | 7/2003 | Chen et al. | |
| 6,605,038 B1 | 8/2003 | Teller et al. | |
| 6,605,044 B2 | 8/2003 | Bimbaum | |
| 6,609,023 B1 | 8/2003 | Fischell et al. | |
| 6,612,984 B1 | 9/2003 | Kerr, II | |
| 6,616,613 B1 * | 9/2003 | Goodman | 600/504 |
| 6,645,154 B2 | 11/2003 | Oka | |
| 6,645,155 B2 | 11/2003 | Inukai et al. | |
| 6,652,466 B2 | 11/2003 | Sugo et al. | |
| 6,676,608 B1 | 1/2004 | Keren | |
| 6,678,543 B2 | 1/2004 | Diab et al. | |
| 6,681,454 B2 | 1/2004 | Modgil et al. | |
| 6,714,804 B2 | 3/2004 | Al-Ali et al. | |
| 6,723,054 B1 | 4/2004 | Baruch et al. | |
| 6,733,447 B2 | 5/2004 | Lai et al. | |
| 6,740,045 B2 | 5/2004 | Amano | |
| 6,775,566 B2 | 8/2004 | Nissila | |
| 6,808,473 B2 | 10/2004 | Hisano et al. | |
| 6,813,511 B2 | 11/2004 | Diab et al. | |
| 6,814,705 B2 | 11/2004 | Kawaguchi | |
| 6,852,083 B2 | 2/2005 | Caro et al. | |
| 6,871,084 B1 | 3/2005 | Kigsley et al. | |
| 7,215,991 B2 * | 5/2007 | Besson et al. | 600/509 |
| 7,486,977 B2 * | 2/2009 | Sweitzer et al. | 600/323 |
| 7,499,739 B2 * | 3/2009 | Sweitzer et al. | 600/323 |
| 7,819,812 B2 * | 10/2010 | John et al. | 600/504 |
| 2001/0047127 A1 * | 11/2001 | New et al. | 600/300 |
| 2002/0183627 A1 | 12/2002 | Nishii et al. | |
| 2004/0030261 A1 | 2/2004 | Rantala | |
| 2004/0260186 A1 | 12/2004 | Dekker et al. | |
| 2005/0101875 A1 * | 5/2005 | Semler et al. | 600/509 |

OTHER PUBLICATIONS

'Pulse transit time measured from the ECG: an unreliable marker of beat-to-beat blood pressure', Payne et. al, J. Appl. Physiol 100: 136-141, 2006.

Weijia Cui, Lee E. et al., In Vivo Reflectance of Blood and Tissue as a Function of Light Wavelength, submitted to IEEE Transactions on Biomedical Engineering, vol. 37 No. 6, Jun. 1990.

* cited by examiner

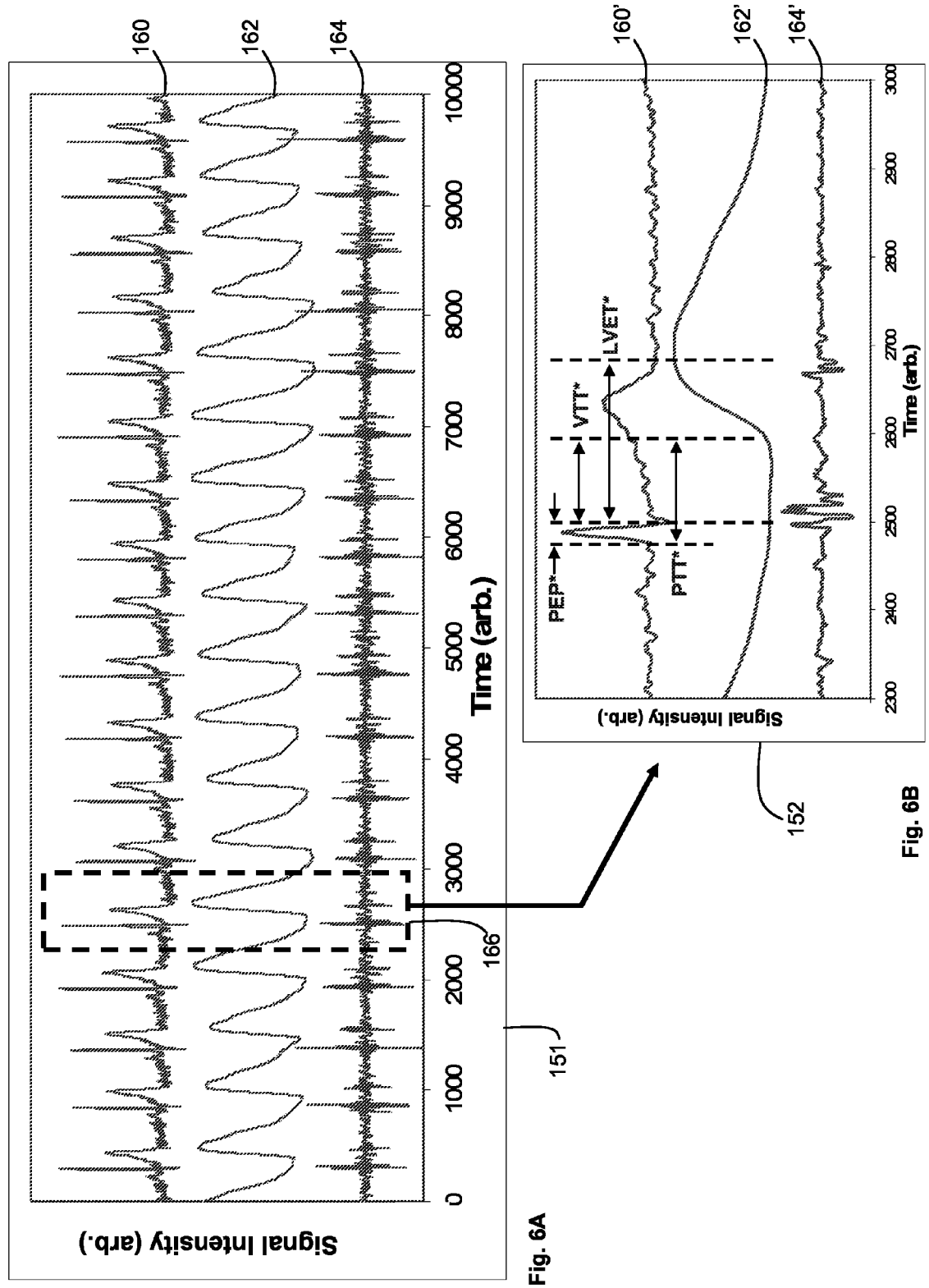

TWO-PART PATCH SENSOR FOR MONITORING VITAL SIGNS

CROSS REFERENCES TO RELATED APPLICATION

Not Applicable

STATEMENT REGARDING FEDERALLY SPONSORED RESEARCH OR DEVELOPMENT

Not Applicable

BACKGROUND OF THE INVENTION

1. Field of the Invention

The present invention relates to medical devices for monitoring vital signs, e.g. blood pressure.

2. Description of the Related Art

Pulse transit time ('PTT'), defined as the transit time for a pressure pulse launched by a heartbeat in a patient's arterial system, has been shown in a number of studies to correlate to both systolic and diastolic blood pressure. In these studies PTT is typically measured with a conventional vital signs monitor that includes separate modules to determine both an electrocardiogram (ECG) and pulse oximetry. During a PTT measurement, multiple electrodes typically attach to a patient's chest to determine a time-dependent ECG characterized by a sharp spike called the 'QRS complex'. This feature indicates an initial depolarization of ventricles within the heart and, informally, marks the beginning of the heartbeat. Pulse oximetry is typically measured with a clothespin-shaped device that clips to the patient's index finger, and includes optical systems operating in both the red and infrared spectral regions. In addition to measuring a pulse oximetry value, this method yields a time-dependent waveform, called a plethysmograph, that indicates both heart rate and a time-dependent volumetric change in an underlying artery (e.g. in the finger) caused by the propagating pressure pulse.

In many studies PTT is calculated from the time separating the onset of the QRS complex to the foot of the plethysmograph. Alternatively, PTT can be calculated as the time separating signals measured by two sensors (e.g. optical or pressure sensors), each sensitive to the propagating pressure pulse, placed at different locations on the patient's body. In both cases, PTT depends primarily on arterial tone, arterial compliance, the propagation distance (closely approximated by the patient's arm length), and of course blood pressure. Typically a high blood pressure results in a shorter PTT.

A number of issued U.S. patents describe the relationship between PTT and blood pressure. For example, among others, U.S. Pat. Nos. 5,316,008; 5,857,975; 5,865,755; and 5,649,543 each teach an apparatus that includes conventional sensors that measure an ECG and plethysmograph that are processed to measure PTT. U.S. Pat. Nos. 6,511,436; 6,599,251; and 6,723,054 each teach an apparatus that includes a pair of optical or pressure sensors, each sensitive to a propagating pressure pulse, that measure PTT. As described in these patents, a microprocessor associated with the apparatus processes the PTT value to estimate blood pressure.

PTT-based measurements of blood pressure are complicated by a number of factors, one of which is the many time-dependent processes associated with each heartbeat that may correlate in a different way with blood pressure, or in fact may not correlate at all. For example, prior to the initial depolarization of the ventricles (marked by the QRS complex), the mitral valve opens and lets blood flow from the left atrium into the left ventricle. This causes the ventricle to fill with blood and increase in pressure. After the onset of the QRS, the mitral valve closes and the aortic valve opens. When the heart contracts, blood ejects into the aorta until the aortic valve closes. The time separating the onset of the QRS and the opening of the aortic valve is typically called the pre-injection period, or 'PEP'. The time separating opening and closing of the aortic valve is called the left ventricular ejection period, or 'LVET'. LVET and PEP, along with additional time-dependent properties associated with each heartbeat, are typically included in a grouping of properties called systolic time intervals, or 'STIs'.

PTT and LVET can be measured with a number of different techniques, such as impedance cardiography ('ICG') and by measuring a time-dependent acoustic waveform, called a phonocardiogram ('PCG'), with an acoustic sensor. The PCG, characterized by acoustic signatures indicating the closing (and not opening) of the mitral and aortic valves, is typically coupled with an ECG to estimate PEP and LVET. For example, U.S. Pat. Nos. 4,094,308 and 4,289,141 each teach an apparatus that measures a PCG and ECG, and from these waveforms estimates PEP and LVET. U.S. Pat. No. 7,029,447 teaches an apparatus using transit times calculated from an ICG measurement to determine blood pressure.

Studies have also shown that a property called vascular transit time ('VTT'), measured from features in both a PCG and plethysmograph, can correlate to blood pressure. Such a study, for example, is described in an article entitled 'Evaluation of blood pressure changes using vascular transit time', *Physiol. Meas.* 27, 685-694 (2006). In addition, studies have shown that PEP and LVET, taken alone, can correlate to blood pressure. These studies typically require multiple sensors placed on the patient's body to measure time-dependent waveforms that are processed to determine PEP and LVET. Studies that relate these properties to blood pressure, for example, are described in 'Systolic Time Intervals in Man', *Circulation* 37, 149-159 (1968); 'Relationship Between Systolic Time Intervals and Arterial Blood Pressure', *Clin. Cardiol.* 9, 545-549 (1986); 'Short-term variability of pulse pressure and systolic and diastolic time in heart transplant recipients', *Am. J. Physiol. Heart Circ. Physiol.* 279, H122-H129 (2000); and 'Pulse transit time measured from the ECG: an unreliable marker of beat-to-beat blood pressure', *J. Appl Physiol.* 100, 136-141 (2006).

SUMMARY OF THE INVENTION

The sensor according to this invention makes cuffless blood pressure measurements using a two-part patch sensor featuring a disposable component that includes a pair of electrodes and a non-disposable component that features optical and acoustic sensors. When snapped together, the disposable and non-disposable components form an adhesive sensor with a form factor similar to a conventional band-aid that typically attaches to a patient's chest, just below their sternal notch. During operation, the sensor measures optical, electrical, and acoustic waveforms from the patient, which a microprocessor then analyzes as described in detail below to determine blood pressure and other vital signs. In this way, the sensor replaces a conventional cuff to make a rapid measurement of blood pressure with little or no discomfort to the patient.

Specifically, in one aspect, the invention provides system for monitoring blood pressure from a patient that includes a patch sensor component featuring: i) a backing material comprising a first opening; and ii) first and second electrodes, each electrode connected to the backing material and including an electrical lead and a conductive electrode material. The electrode generates an electrical signal that passes through the electrical lead when the conductive electrode material contacts the patient. The patch sensor component connects to a circuit board component that includes: i) first and second connectors that connect to the first and second electrical leads to receive the first and second electrical signals; and ii) an optical component, featuring a light source photodetector, that detects the optical radiation after it irradiates the patient to generate an optical waveform. The optical component inserts into the first opening of the patch sensor component when the first and second connectors connect, respectively, to the first and second electrical leads. A monitoring device, connected to the circuit board component by a cable, receives and process the optical waveform (or a processed version thereof) and the first and second electrical signals (or processed versions thereof) to determine blood-pressure information.

The patient typically wears the sensor on or just below the 'sternal' notch of their chest, proximal to their heart. In this location the sensor simultaneously measures optical, electrical, and acoustic signals. These signals are then processed with an algorithm described below to measure blood pressure and other vital signs. The measurement is possible because: 1) the proximity of this area to the heart allows the acoustic sensor to measure acoustic signals caused by closure of the mitral and aortic valves; 2) an abundance of capillaries in the sternal notch, meaning optical signals can be measured in a reflective mode; and 3) the strong electrical activity of the heart in this area, meaning electrical signals can be measured with a high signal-to-noise ratio even when the electrodes are relatively close together.

In embodiments, the first and second electrodes removably connect, respectively, to first and second portions of the backing material, and the first opening that receives the optical component is disposed between the first and second portions. Typically both the first and second electrical leads comprise a metal snap component, e.g. a substantially cylindrical 'male' component configured to snap into a 'female' connector on the circuit board component. In embodiments, the metal snap component comprises an Ag/AgCl coating and the conductive electrode material comprises a conductive solid or liquid gel. The combination of these materials is known in the art to improve the quality of electrical signals collected from the patient.

In other embodiments, the backing material comprises a flexible foam material and is coated on one side with an adhesive layer. Typically the adhesive layer is designed to effectively secure the sensor to the patient's skin, and is covered with a protective plastic coating when the sensor is not in use. This keeps both the adhesive layer and solid or liquid gel from drying out.

The backing material typically includes a second opening, with the acoustic sensor configured to insert into the second opening when the first and second connectors on the backing material connect, respectively, to the first and second electrical leads. To increase coupling of acoustic signals into the acoustic sensor, the backing material can additionally include an impedance-matching gel disposed over the second opening. During use, the electrical leads of the patch sensor component snap into their mated connectors on the circuit board component, and the acoustic sensor inserts into the second opening and contacts the impedance-matching gel. The impedance-matching gel is sandwiched between the acoustic sensor and the patient's skin when the two-part sensor is attached to the patient. This improves coupling of acoustic signals into the acoustic sensor, thereby increase the quality of the measured signal.

In another aspect, the invention provides a system for measuring blood pressure values that features a main component comprising an optical sensor, an acoustic sensor, a first receptor, and a second receptor. A disposable component removably attaches to the main component. The disposable component features: i) a polymeric body with an exterior surface and an interior surface coated with an adhesive film; ii) a first electrode; iii) a second electrode; iv) a first aperture; and v) a second aperture. During use, the optical sensor extends through the first aperture, the acoustic sensor extends through the second aperture, and the first and second electrodes connect to, respectively, the first and second receptors of the main component. A processing device calculates a real-time blood pressure value from the electrical signals from the first and second electrodes, an optical signal from the optical sensor, and an acoustic signal from the acoustic sensor.

The invention has many advantages. In particular, it provides a low-profile, disposable sensor that measures a variety of vital signs, particularly blood pressure, without using a conventional cuff. This and other information can be transferred to a central monitor through a wired or wireless connection to better characterize a patient. For example, with the system a medical professional can continuously monitor a patient's blood pressure and other vital signs during their day-to-day activities. Monitoring patients in this manner increases patient care and the accuracy of a blood-pressure measurement while minimizing erroneous measurements due to, e.g., 'white coat syndrome'.

Once collected, information describing the blood pressure can be viewed using an Internet-based website, a personal computer, or simply by viewing a display on the device. Blood-pressure information measured continuously throughout the day provides a relatively comprehensive data set compared to that measured during isolated medical appointments. This approach identifies trends in a patient's blood pressure, such as a gradual increase or decrease, which may indicate a medical condition that requires treatment. The system also minimizes effects of 'white coat syndrome' since the monitor automatically and continuously makes measurements away from a medical office with basically no discomfort to the patient.

These and other advantages are described in detail in the following description, and in the claims.

BRIEF DESCRIPTION OF THE DRAWINGS

FIG. 6A is a graph of time-dependent electrical, optical, and acoustic waveforms measured with the two-part patch sensor connected to the patient in FIG. 5A;

FIG. 6B is a graph of the time-dependent electrical, optical, and acoustic waveforms shown in FIG. 6A plotted over a relatively short time scale;

DETAILED DESCRIPTION OF THE INVENTION

Figure 1:
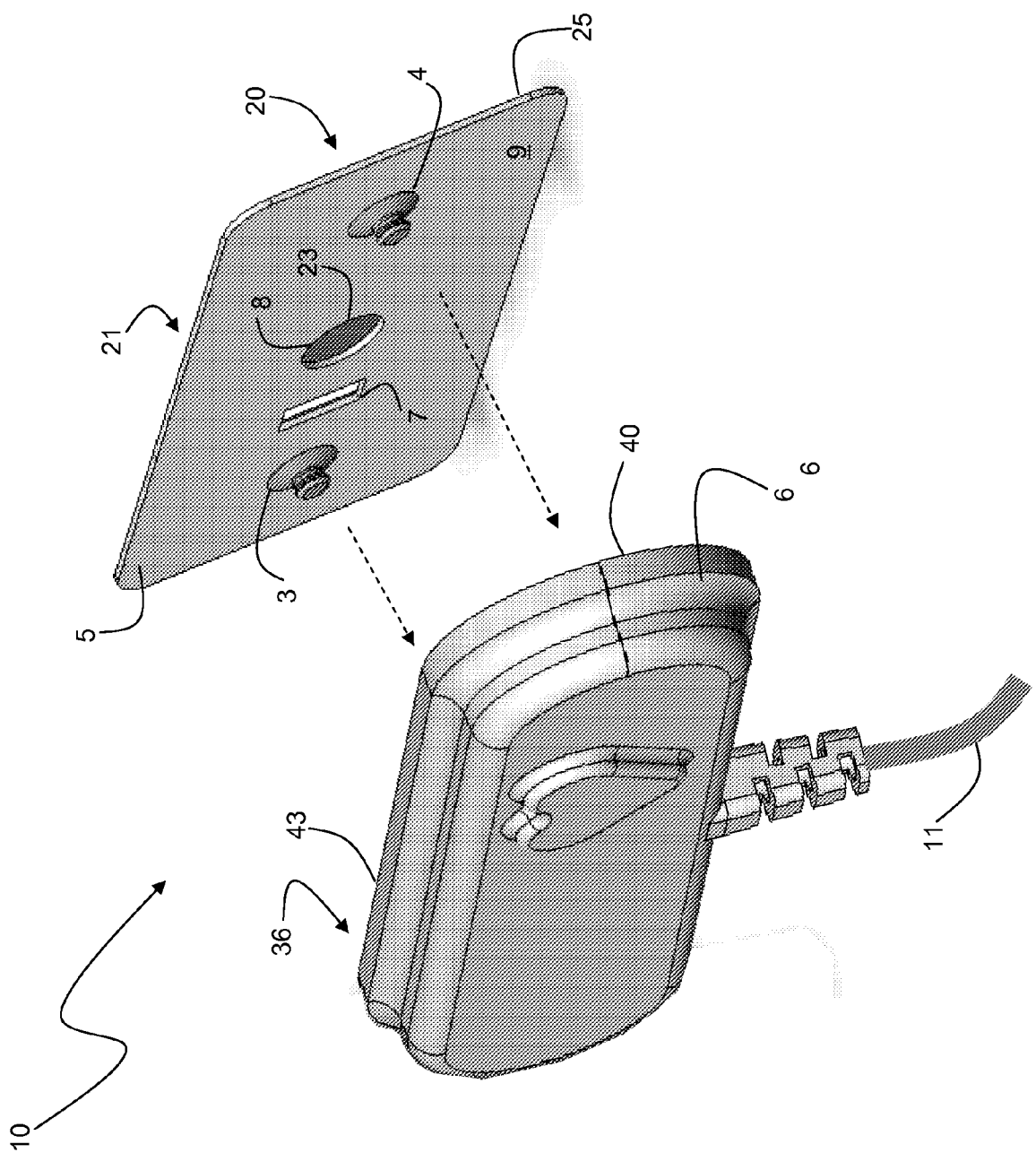
FIG. 1 is an exploded view of the two-part patch sensor according to the invention wherein the non-disposable sensor housing connects to the disposable patch sensor.
Figure 2:
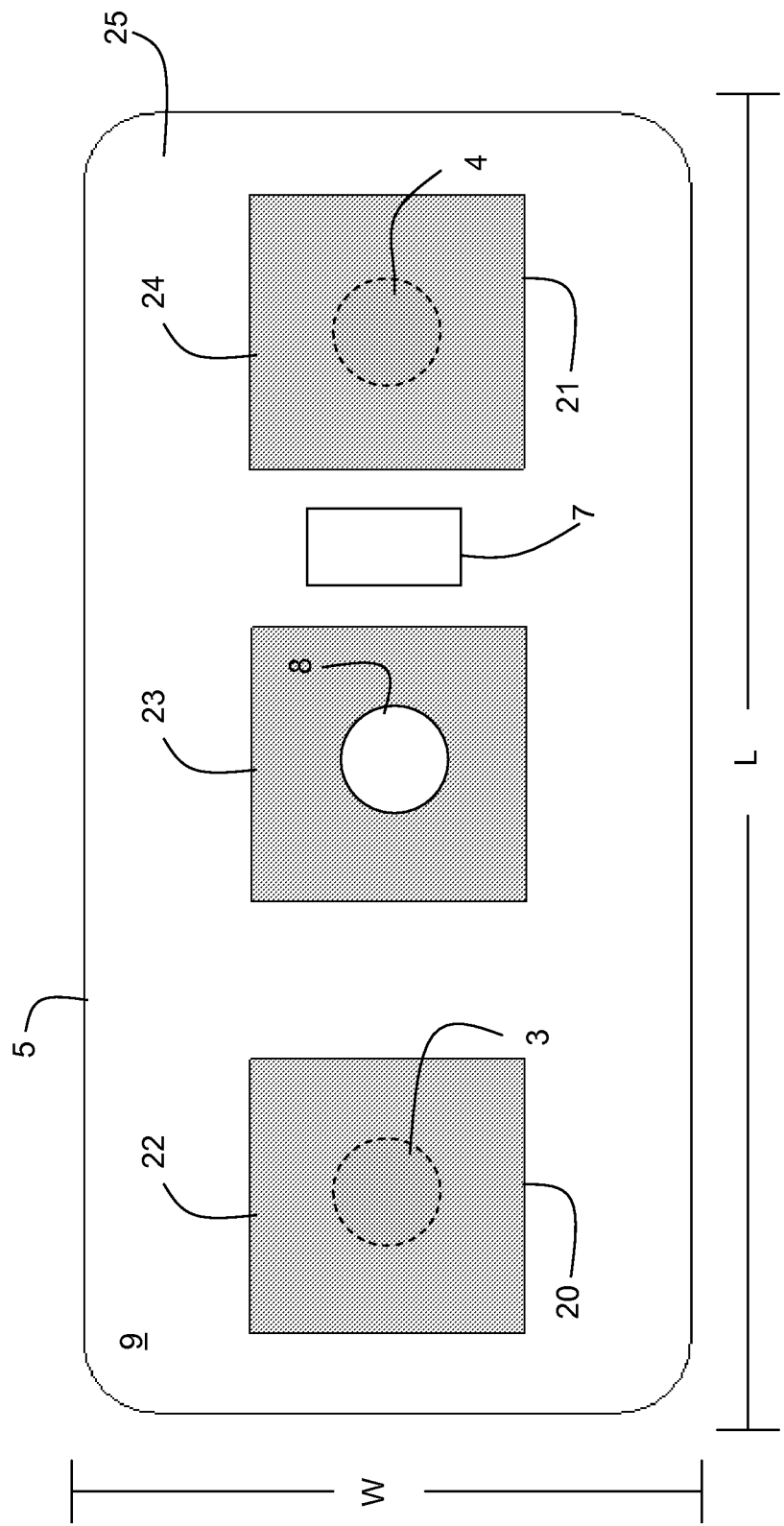
FIG. 2 is a front view of the disposable patch sensor of FIG. 1.
Figure 3:
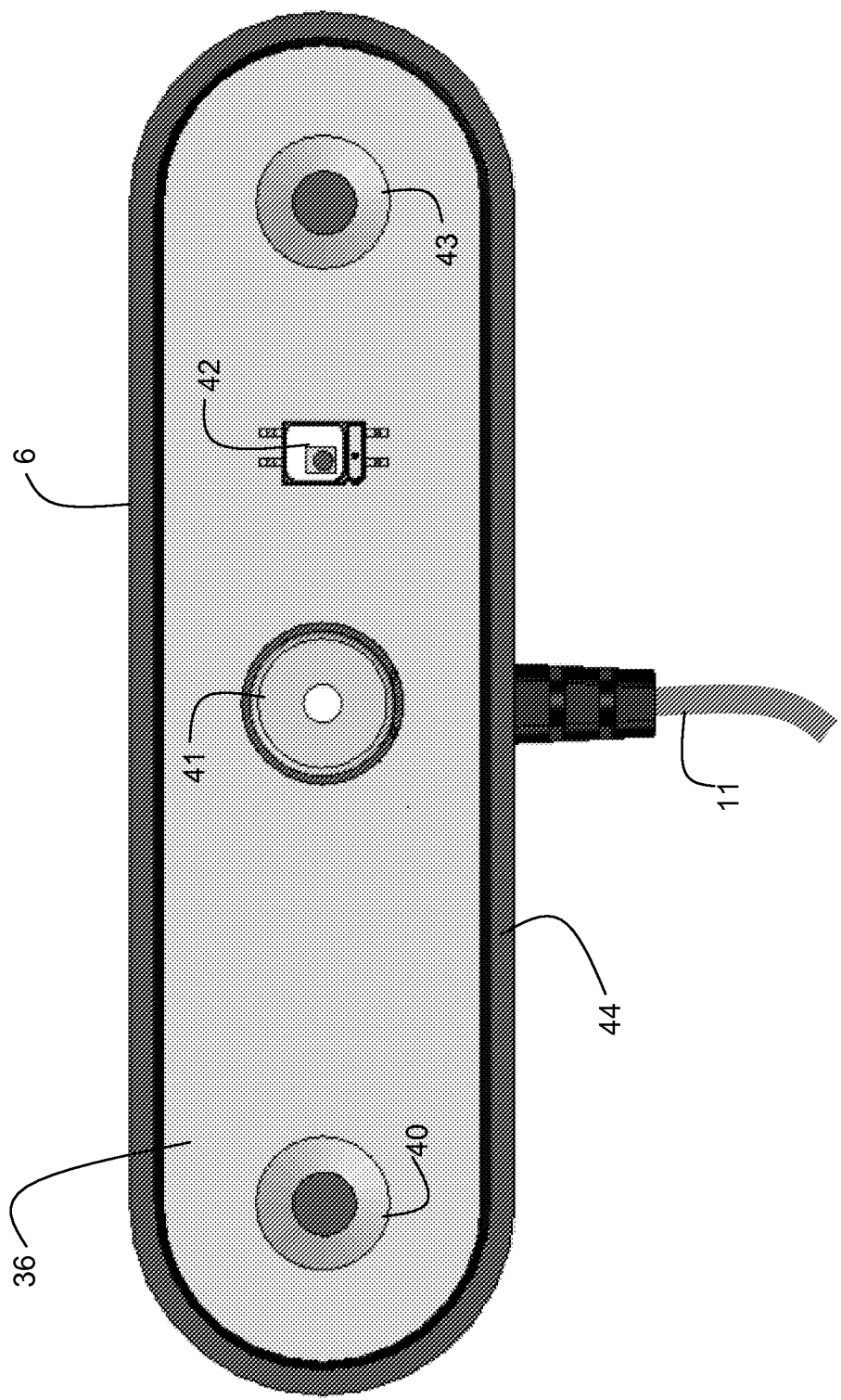
FIG. 3 is a front view of the non-disposable sensor housing of FIG. 1 containing a sensor board.

FIGS. 1, 2, and 3 show a two-part patch sensor 10 according to the invention that features a disposable adhesive patch sensor 5 that attaches to a non-disposable sensor housing 6 to measure optical, electrical, and acoustic waveforms from a patient's chest. The optical, acoustic and electrical waveforms represent, respectively, capillary blood flow, mitral and aortic valve closures, and electrical activity generated by the patient's heart. A cable 11 containing a shielded wire for each signal transports the waveforms to a main console (the components of which are shown in FIG. 8) that processes them to measure a patient's vital signs, particularly blood pressure. One such processing technique, for example, is described in detail in co-pending U.S. patent application Ser. No. 11/470,708, entitled Hand-Held Vital Signs Monitor, filed Sep. 7, 2006, the pertinent contents of which are hereby incorporated by reference.

The patch sensor 5 features a sterile backing 9 composed of a polymeric material (e.g. foam) that supports electrodes 20, 21 and makes measurements by adhering to a patient's skin; after use it is discarded. The sensor housing 6 encloses a circuit board component 36 that supports solid-state, non-disposable optical 42 and acoustic 41 sensors, described in detail below, and is designed to be used with multiple disposable patch sensors. The patch sensor 5 contains primary 20 and a secondary 21 electrodes, each composed of a cylindrical 'male' electrical lead 3, 4 coated with Ag/AgCl that snaps into a mated female connector 40, 43 on the sensor board 6. The electrical leads 3, 4 contain a bottom portion that extends through the foam backing 9 and contacts a conductive 'solid gel' 22, 24 that sticks to the patient during operation. The solid gel 22, 24 has an electrical impedance (approximately 100,000 ohms*cm) that approximates the patient's skin to improve coupling of electrical signals into the electrodes 20, 21.

The sterile foam backing 9 (approximate dimensions: L~9 cm, W~4.5 cm, T~0.1 cm) includes clear apertures 7, 8 positioned to match the orientation and geometry of, respectively, the optical 42 and acoustic 41 sensors surface-mounted on the circuit board component 36. The clear aperture 8 for the acoustic sensor 41 is additionally covered by a non-conductive, water-based solid gel 23 that approximates the acoustic impedance of the patient's skin to improve coupling of acoustic signals from the patient into the acoustic sensor 41. The foam's back surface is coated with a non-allergenic adhesive 25 so that it securely sticks to the patient's skin during operation. Before the patch sensor 5 is used, a thin, plastic adhesive backing (not shown in the figure) covers the adhesive 25 and the solid gels 22, 23, 24 to prevent them from drying out.

Figure 5B:
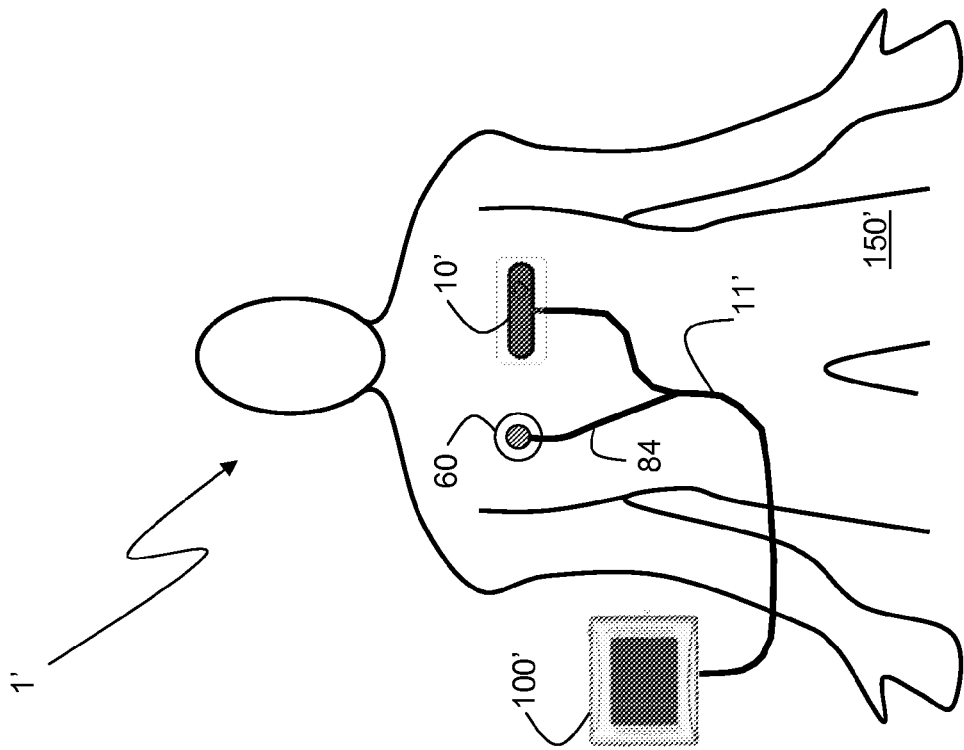
FIG. 5B is a schematic view of the two-part patch sensor of FIG. 1 and the secondary electrode of FIG. 4B connected to a patient's chest.
Figure 5A:
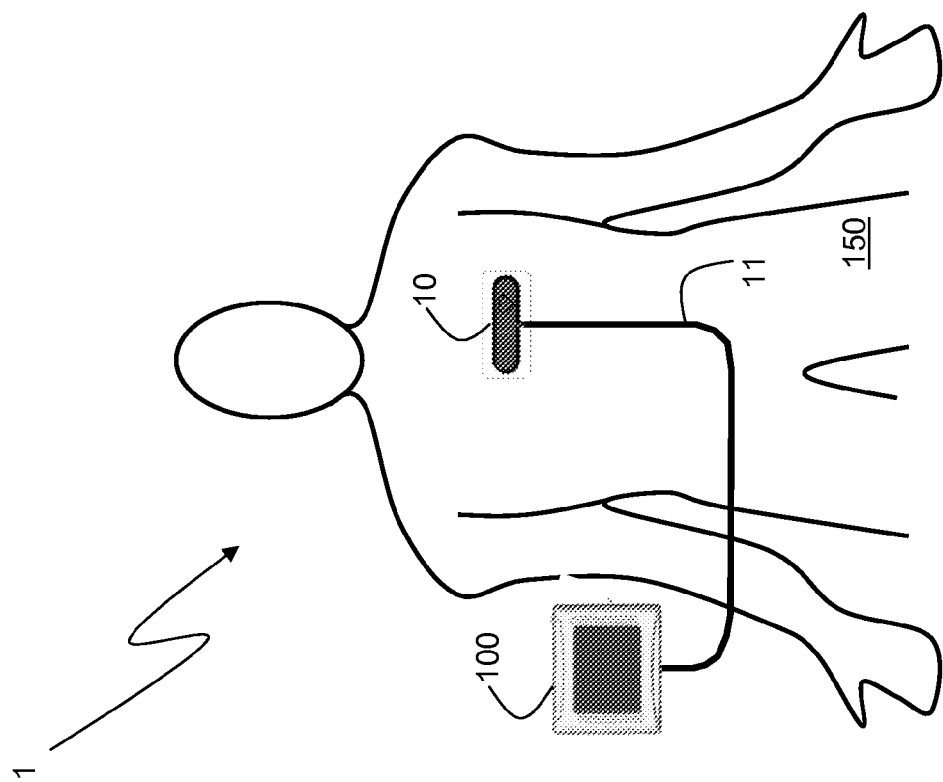
FIG. 5A is a schematic view of the two-part patch sensor of FIG. 1 connected to a patient's chest.

During operation a medical professional snaps the male electrical leads 3, 4 of the patch sensor 5 into the female snap connectors 43, 40 on the circuit board component 36. This action secures the sensor housing 6 and circuit board component 36 to the disposable patch sensor 5 and presses the acoustic 41 and optical 42 sensors through, respectively, the clear holes 8, 7 on the foam backing 9. The optical sensor 42 presses completely through its clear hole 7 and is exposed so that it directly contacts the patient's skin, whereas the acoustic sensor 41 presses partially through its clear hole 8 and contacts the non-conductive solid gel 23. The medical professional then peels off the protective backing and sticks the combined patch sensor 10, featuring the non-disposable housing 6, circuit board component 36, and disposable patch sensor 5, onto the patient. To make a measurement, the optical sensor 42 and electrodes 20, 21 each contact the patient directly, while the acoustic sensor 41 contacts the impedance-matched solid gel 23, which in turn contacts the patient. As shown in FIG. 5A, the patch sensor 10 preferably attaches to the patient 150 just below their sternal notch, and connects to a console 100 typically located proximal to the patient 150. The sternal notch, as described above, is an ideal location wherein the patch sensor 10 can effectively measure optical, electrical, and acoustic signals.

Figure 4B:
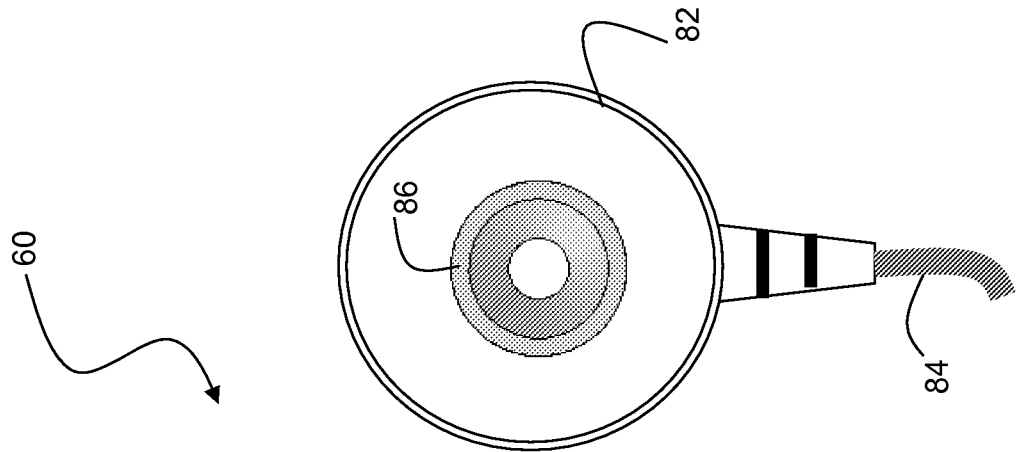
FIG. 4B is a front view of a secondary electrode connector that connects to the secondary electrode of FIG. 4A.
Figure 4A:
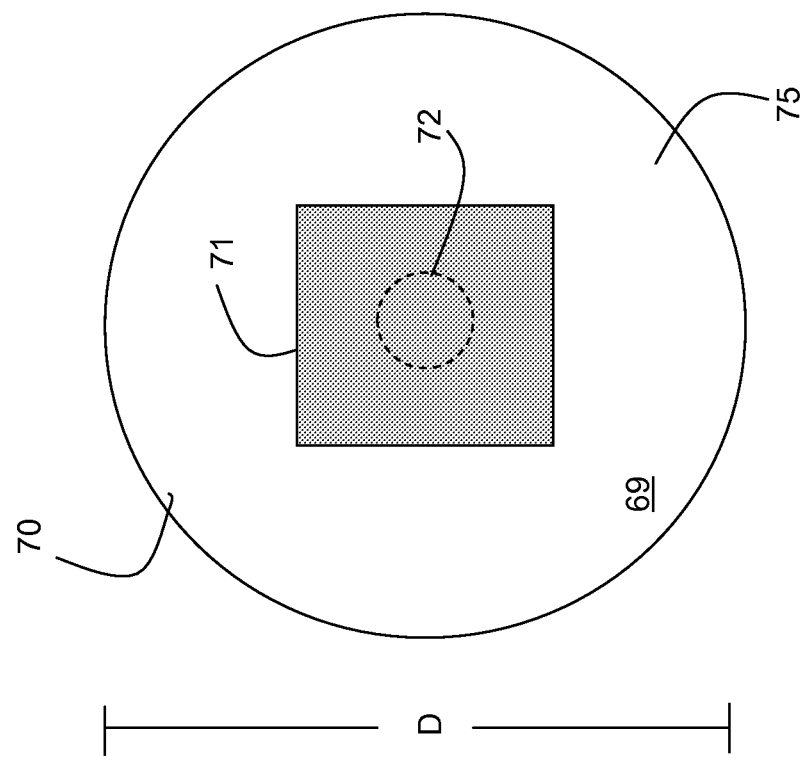
FIG. 4A is a schematic front view of an external, secondary electrode that connects to the two-part patch sensor of FIG. 1 to improve the quality of the electrical waveform.

To improve the quality of the electrical waveform, the two-part patch sensor 10 may connect to a secondary two-part electrode 60, shown in FIGS. 4A and 4B, which is similar to a conventional ECG electrode. The two-part electrode 60 features a disposable electrode 70 that, like the disposable patch sensor shown in FIGS. 1-3, includes a sterile foam backing 69 that supports an Ag/AgCl-coated male electrical lead 72 that contacts an impedance-matching solid gel 71. An adhesive layer 75 coats the foam backing 69 so that it sticks to the patient's skin. During use, the male electrical lead 72 snaps into a female snap connector 86 housed by a secondary electrode connector 82. A shielded cable 84 connects the secondary two-part electrode 60 to the primary two-part patch sensor described above. In a preferred embodiment, electrodes 20, 21 measure, respectively, a positive signal and ground signal, while the two-part electrode 60 measures a negative signal. An electrical amplifier in the main console then processes the positive, negative, and ground signals to generate an electrical waveform, described in detail below, that is similar to a single-lead ECG. FIG. 5B, for example, shows how the secondary two-part electrode 60 connects to the two-part patch sensor 10' through the cable 84; the combined system then attaches to a patient 150' and connects to the console 100' through a cable 11' to measure the patient's vital signs.

FIGS. 6A and 6B show graphs 151, 152 of the time-dependent electrical waveform 160, optical waveform 162, and acoustic waveform 164 measured by the above-described sensors. Each waveform 160, 162, 164 includes time-dependent features that repeat with each heartbeat. For example, the electrical waveform 160 looks similar to a conventional ECG and features a QRS complex featuring a sharp spike that indicates an initial depolarization of the ventricle. Because of its well-defined features, the QRS complex is relatively easy to detect with a computational algorithm, and serves as an effective 'marker' that indicates each individual heartbeat. The optical waveform 162 is measured from underlying capillaries in the patient's chest and features a slowly varying pulse that indicates an increase in volume in the capillaries caused by a propagating pressure wave. Finally, the acoustic waveform features two 'beats', each representing a collection of acoustic frequencies, that occur with each heartbeat. The first and second beats represent the sounds made following closure of, respectively, the heart's mitral and aortic valves; these are the conventional 'lub' and 'dub' heard through a stethoscope.

FIG. 6B graphs a portion of the waveforms highlighted by a box 166 of FIG. 6A, and indicates how a microprocessor preferably analyzes the various features of the electrical waveform 160', optical waveform 162', and acoustic waveform 164' to determine a variety of systolic time intervals. These systolic time intervals are then further processed to determine a patient's real-time blood pressure. Co-pending U.S. patent application Ser. No. 11/470,708, entitled Hand-Held Vital Signs Monitor and filed Sep. 7, 2006, previously incorporated herein by reference, describes this processing method in detail. As described above, the QRS complex in the electrical waveform 160', which is caused by initial depolarization of the heart muscle, serves as a marker indicating the start of each heart beat. At a later time, the mitral valve opens and blood flows from the heart's left atrium into the left ventricle. The mitral valve then closes, causing the first beat in the acoustic waveform 164', and the aortic valve opens shortly thereafter. The opening of the aortic valve does not result in a feature in the acoustic waveform 164' (only closing valves do this), but is assumed to follow within approximately 10 milliseconds after the closing of the mitral valve. The time difference between the onset of the QRS complex and the opening of the aortic valve is called the 'pre-injection period', or PEP. Since the technique described herein does not explicitly measure the opening of the aortic valve, but rather the closure of the mitral valve, it is labeled PEP*. Once the aortic valve opens, the heart pumps a bolus of blood through the aorta, resulting in a pressure wave that propagates through the patient's arterial system. The propagation time of the pressure wave is a strong function of the patient's blood pressure, along with their vascular compliance and resistance. When the pressure wave reaches capillaries in the patient's chest, the rise in pressure causes the capillaries to increase in volume with blood, which in turn increases the amount of optical radiation from the LED of the optical sensor 20 that the flowing blood absorbs. The photodetector in the optical sensor 20 detects this as a time-dependent pulse characterized by a relatively sharp rise time and a slower decay, as indicated by the optical waveform 162'. The time difference between the estimated opening of the aortic valve and the onset of the pulse's rise time is the 'vascular transit time' (VTT*). Typically the VTT* decreases with higher blood pressure. The second beat in the acoustic waveform 164' represents the closure of the aortic valve, and the time period separating this from the estimated opening of the aortic valve is called the 'left ventricular ejection period' (LVET*). Finally, the onset of the QRS complex and the foot of the plethysmograph is the pulse transit time (PTT*). Note that the transit time essentially represents the time from when the heart begins to beat to when the pressure wave appears underneath the optical sensor 20. To reach this point, the vascular pathway that the pressure wave must travel is somewhat complicated: it extends through the aorta, the subclavian artery, a series of smaller arteries proximal to the patient's ribs, and finally through relatively small capillaries attached to these arteries.

Other properties known to correlate to blood pressure can also be measured from the optical waveform 162, electrical waveform 160, and acoustic waveform 164. For example, the rise and fall times of the optical waveform 162 can meet this criterion, and thus these properties can be measured from the optical waveform 162. In addition, in some cases the optical waveform 162 will include a primary and secondary peak, separated by a feature called the 'dicrotic notch'. The microprocessor can be programmed to take a second derivative of the waveform to determine the ratio of the primary and second peaks, and this property has been shown to correlate to blood pressure. In addition, variability in the patient's heartbeat, as measured from each of the electrical waveform 160, optical waveform 162, and acoustic waveform 164, can indicate variation in the patient's blood pressure, and can also be processed by the microprocessor. Heart rates from these three waveforms can be calculated and averaged together to yield a very accurate measure of the patient's real-time heart rate.

Figure 7:
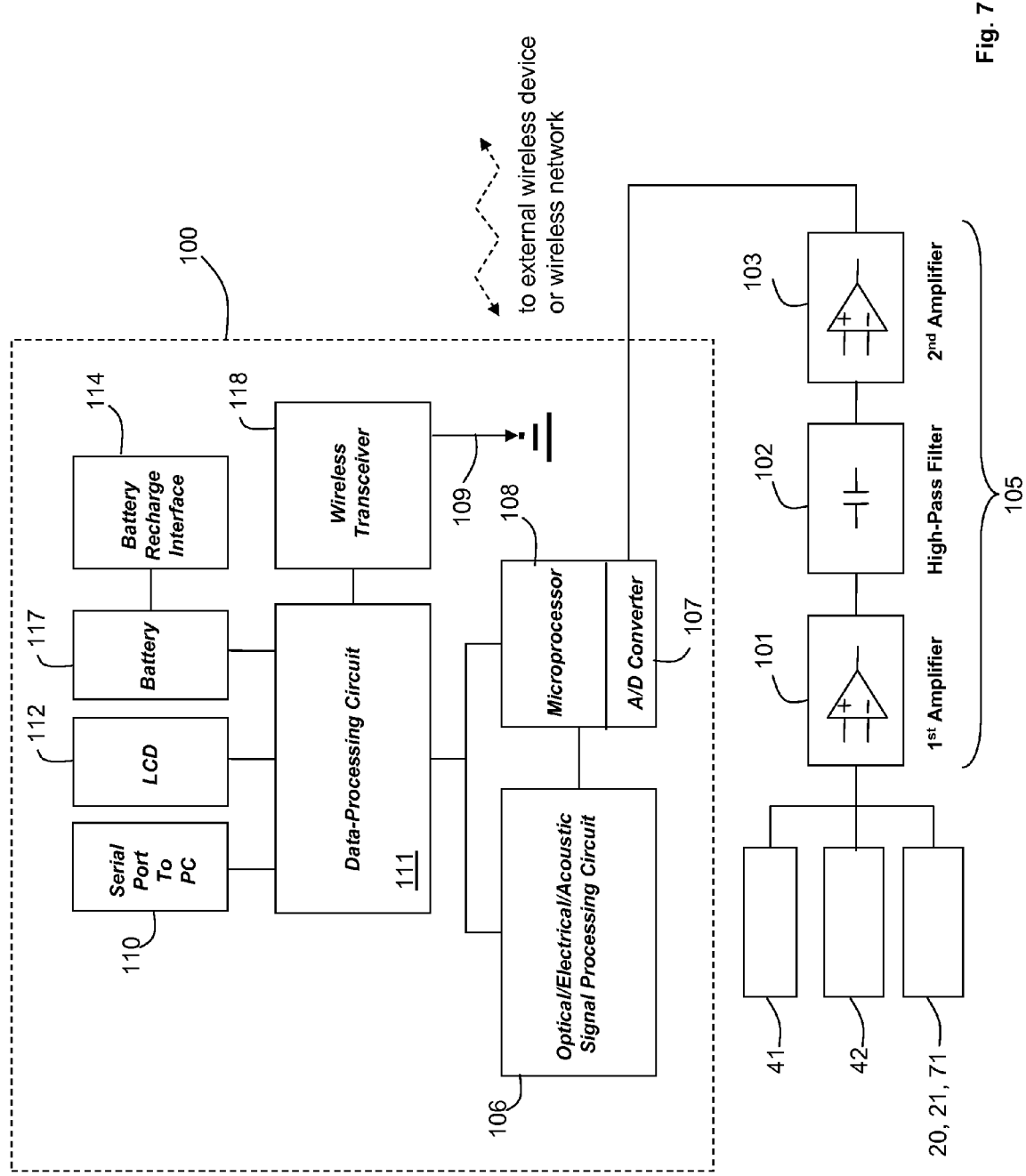
FIG. 7 is a schematic diagram of processing components used to process waveforms measured by the two-part patch sensor of FIG. 1 to determine a patient's blood pressure.

FIG. 7 shows a preferred configuration of electronic components featured within the console 100 that process the above-described information to measure a patient's vital signs. A data-processing circuit 111 connects to an optical/electrical/acoustic signal processing circuit 106 that controls the optical sensor 41, acoustic sensor 42, and electrodes 20, 21, 71. During operation, signals from these sensors independently pass through a two-stage amplifier system 105 that includes first 101 and second 103 amplifier stages separated by a high-pass filter 102. A typical circuit board used in this application features a separate two-stage amplifier system 105 for the optical, electrical, and acoustic signals; a single amplifier is shown in FIG. 7 for simplicity. The first 100 and second 103 amplifiers independently amplify analog input signals, while the high-pass filter 102 removes low-frequency noise and DC component in the signals to further improve their quality. Signals that pass through the two-stage amplifier system 105 are then sent to an analog-to-digital converter 107 connected to a microprocessor 108. The analog-to-digital converter 107 can be integrated within the microprocessor 108, or can be an independent chipset. In either case, the analog-to-digital converter 107 digitizes the analog optical, electrical, and acoustic waveforms to generate arrays of data points that can be processed by the microprocessor 108 using the algorithms described above to determine blood pressure, heart rate, and pulse oximetry using techniques described herein and known in the art.

To communicate with external wireless devices and networks, the data-processing circuit 111 connects to a wireless transceiver 118 that communicates through an antenna 109 to a matched transceiver embedded within an external component. The wireless transceiver 118 can be a short-range wireless transceiver, e.g. a device based on 802.11, Bluetooth™, Zigbee™, or part-15 wireless protocols. Alternatively, the wireless transceiver 118 can be a cellular modem operating on a nation-wide wireless network, e.g. a GSM or CDMA wireless network. The data-processing circuit 111 can also display information on a touchable interactive liquid crystal display ('LCD') 112, and transmit and receive information through a serial port 110. A battery 117 powers all the electrical components within the console 100, and is preferably a metal hydride battery (generating 3-7V, and most preferably about 3.7V) that can be recharged through a battery-recharge interface 114.

In addition to those methods described above, a number of additional methods can be used to calculate blood pressure from the optical, electrical, and acoustic waveforms. These are described in the following co-pending patent applications, the contents of which are incorporated herein by reference: 1) CUFFLESS BLOOD-PRESSURE MONITOR AND ACCOMPANYING WIRELESS, INTERNET-BASED SYSTEM (U.S. Ser. No. 10/709,015; filed Apr. 7, 2004); 2) CUFFLESS SYSTEM FOR MEASURING BLOOD PRESSURE (U.S. Ser. No. 10/709,014; filed Apr. 7, 2004); 3) CUFFLESS BLOOD PRESSURE MONITOR AND ACCOMPANYING WEB SERVICES INTERFACE (U.S. Ser. No. 10/810,237; filed Mar. 26, 2004); 4) VITAL SIGN MONITOR FOR ATHLETIC APPLICATIONS (U.S. Ser. No. filed Sep. 13, 2004); 5) CUFFLESS BLOOD PRESSURE MONITOR AND ACCOMPANYING WIRELESS MOBILE DEVICE (U.S. Ser. No. 10/967,511; filed Oct. 18, 2004); and 6) BLOOD PRESSURE MONITORING DEVICE FEATURING A CALIBRATION-BASED ANALYSIS (U.S. Ser. No. 10/967,610; filed Oct. 18, 2004); 7) PERSONAL COMPUTER-BASED VITAL SIGN MONITOR (U.S. Ser. No. 10/906,342; filed Feb. 15, 2005); 8) PATCH SENSOR FOR MEASURING BLOOD PRESSURE WITHOUT A CUFF (U.S. Ser. No. 10/906,315; filed Feb. 14, 2005); 9) PATCH SENSOR FOR MEASURING VITAL SIGNS (U.S. Ser. No. 11/160,957; filed Jul. 18, 2005); 10) WIRELESS, INTERNET-BASED SYSTEM FOR MEASURING VITAL SIGNS FROM A PLURALITY OF PATIENTS IN A HOSPITAL OR MEDICAL CLINIC (U.S. Ser. No. 11/162,719; filed Sep. 9, 2005); 11) HAND-HELD MONITOR FOR MEASURING VITAL SIGNS (U.S. Ser. No. 11/162,742; filed Sep. 21, 2005); 12) CHEST STRAP FOR MEASURING VITAL SIGNS (U.S. Ser. No. 11/306,243; filed Dec. 20, 2005); 13) SYSTEM FOR MEASURING VITAL SIGNS USING AN OPTICAL MODULE FEATURING A GREEN LIGHT SOURCE (U.S. Ser. No. 11/307,375; filed Feb. 3, 2006); 14) BILATERAL DEVICE, SYSTEM AND METHOD FOR MONITORING VITAL SIGNS (U.S. Ser. No. 11/420,281; filed May 25, 2006); 15) SYSTEM FOR MEASURING VITAL SIGNS USING BILATERAL PULSE TRANSIT TIME (U.S. Ser. No. 11/420,652; filed May 26, 2006); 16) HAND-HELD VITAL SIGNS MONITOR, (U.S. Ser. No. 11/470,708, filed Sep. 7, 2006); and, 17) BLOOD PRESSURE MONITOR, (U.S. Ser. No. 11/530,076 filed Sep. 8, 2006).

Other embodiments are within the scope of the invention. For example, FIG. 8A shows an embodiment where a non-disposable sensor component 196 is separated into first 200 and second 205 pieces, both of which connect to a disposable patch component 199 similar to that shown in FIGS. 1 and 2. The disposable patch component 199 includes an adhesive backing that adheres to a patient during a measurement. In this embodiment, the first piece 200 of the non-disposable sensor component includes a soft rubber overmold that covers a female snap connector (not shown in the figure). The female snap connector connects to a matched male electrical lead and electrode (not shown in the figure) that are similar, respectively, to the electrical lead 3 and electrode 20 shown in FIGS. 1 and 2. The second piece 205 includes a similar rubber overmold that covers a female snap connector, optical sensor, and acoustic sensor (also not shown in the figure) similar to the connector 43, optical sensor 42, and acoustic sensor 41 shown in FIG. 3. The second piece 205 connects to a portion of the disposable patch component 199 that includes apertures for the optical and acoustic sensors.

When separated into multiple components, the non-disposable sensor component 196 is less rigid than that shown in FIG. 3, and thus better conforms to contours in the patient's chest. This allows the optical, acoustic, and electrical sensors to be closely coupled to the patient's body when attached to the disposable patch component 199, thereby improving the quality of the waveforms collected during a measurement. The female snap connector holds the optical and acoustic sensors in place for the measurement, during which the corresponding waveforms are collected and passed through a bifurcated cable 197 that attaches to a processing device (not shown in the figure) similar to the processing device 100 shown in FIG. 5A. A secondary two-part electrode, similar to the electrode 60 shown in FIG. 5B, connects to the processing device through a separate cable to improve the signal-to-noise ratio of the electrical waveform. The processing device processes the waveforms as described above to determine the patient's blood pressure. An additional foam adhesive patch covering top portions of the first 200 and second 205 pieces may be used in this embodiment to further secure these pieces of the non-disposable sensor component to the patient.

Figure 8B:
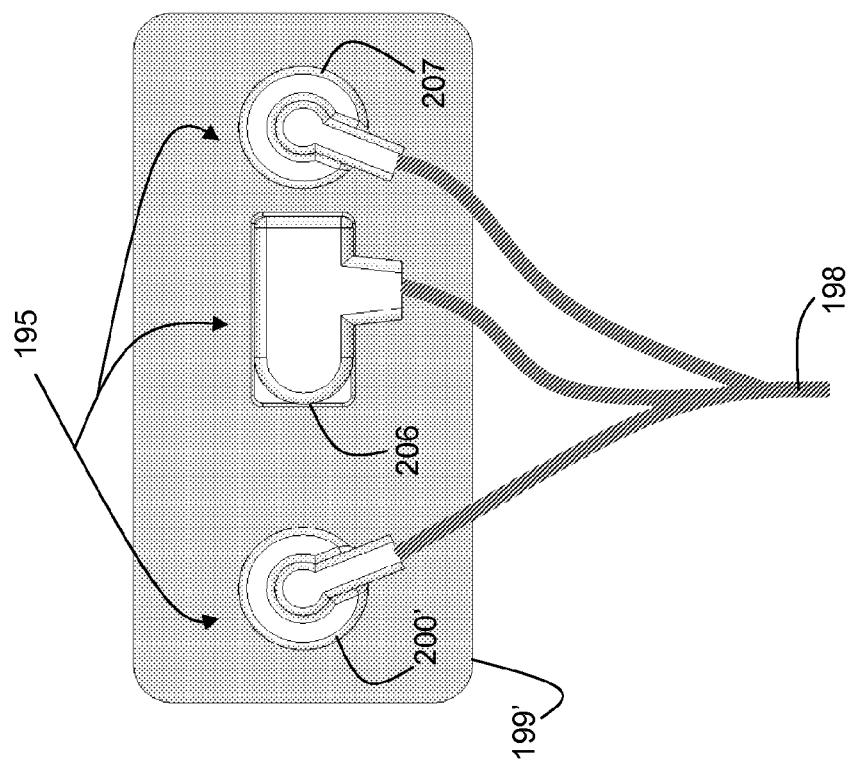
FIG. 8A is a schematic view of a two-piece, non-disposable sensor housing attached to a disposable patch; and, FIG. 8B is a schematic view of a three-piece, non-disposable sensor housing attached to a disposable patch.
Figure 8A:
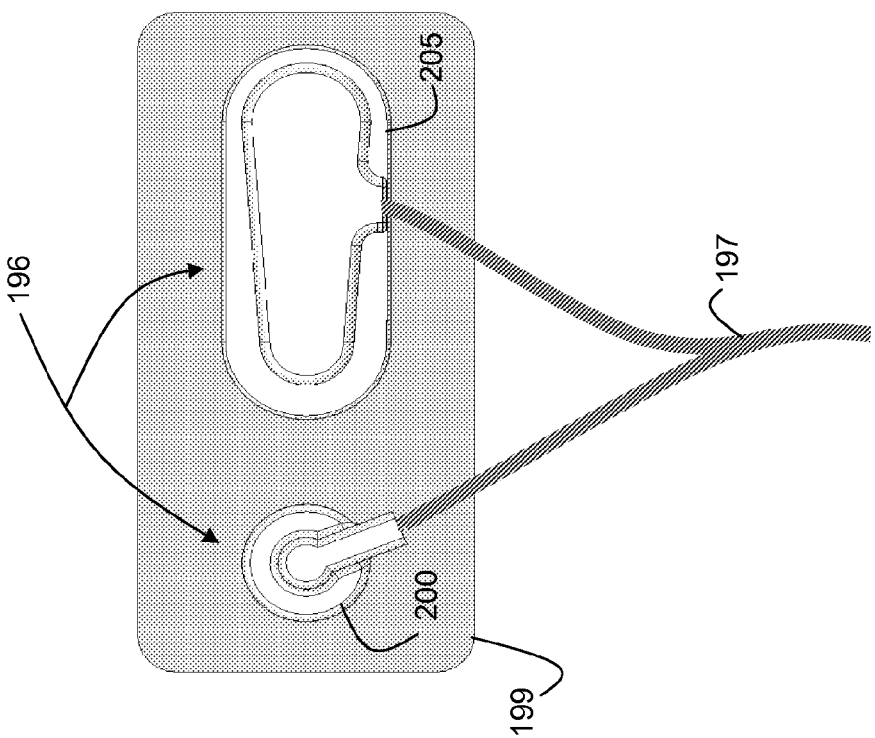

FIG. 8B shows a related embodiment of a non-disposable sensor 195 separated into three separate pieces 200', 206, 207 that attaches to a disposable patch sensor component 199' that adheres to a patient during a measurement. Segmenting the sensor 195 in this way further improves its flexibility and the manner in which it couples to contours in a patient's chest during a measurement. In this embodiment the first 200' and third 207 pieces of the non-disposable sensor 195 include a soft rubber overmold that covers a female snap connector (not shown in the figure) that connect to a matched male electrical lead and electrode (not shown in the figure) similar to that described above. A trifurcated cable 198 connects the non-disposable sensor 195 to a processing device (not shown in the figure) similar to the processing device 100 shown in FIG. 5A.

During a measurement, the first 200' and third 207 pieces snap into their mated connectors and are held firmly in place. The second piece 206 includes a similar rubber overmold that covers optical and acoustic sensors described above. This piece 206 loosely attaches to a portion the disposable sensor 199' that includes apertures for the optical and acoustic sensors, and is further secured using an additional foam adhesive patch. A secondary electrode similar to that described above also connects to the processing device. Once secured to the patient, optical, acoustic, and electrical sensors measure waveforms that pass through the cable 198 to the processing device, which then processes them as described above to determine the patient's blood pressure.

In still other embodiments, each piece of the three-part non-disposable sensor described above connects to a separate disposable sensor. In this embodiment, for example, the first 200' and third 207 pieces of the non-disposable sensor 195 (i.e., the pieces that include a female snap connector) connect to a standard, disposable ECG electrode that includes an adhesive foam backing, Ag/AgCl-coated snap connector, and solid gel. The second piece 206 (i.e. the piece that includes the optical and acoustic sensor) connects to a disposable foam substrate with an adhesive backing that includes apertures for the optical and acoustic sensors.

In still other embodiments, the second piece 205 of the above-mentioned sensor described with reference to FIG. 8A, or the second piece 206 of the above-described sensor described with reference to FIG. 8B, includes only the optical sensor or the acoustic sensor, but not both sensors.

In still other embodiments, the disposable portion of the sensor includes the electrodes, and is a separate component that simply adheres with an adhesive to the non-disposable portion that includes the optical and acoustic sensors and a cable that connects to the console. In this case the disposable and non-disposable portions include matched electrical contacts that touch each other when the two portions are adhered. This way electrical signals measured by the electrodes can be passed to the non-disposable portion and through the cable to the console, where they are processed to determine the electrical waveform.

Other embodiments are also within the scope of the invention.

We claim as our invention the following:

1. A system for measuring blood pressure values for a user, the system comprising:
   a monitoring component comprising:
      a main component comprising an optical sensor, an acoustic sensor, first receptor and second receptor,
      a disposable component removably attachable to the main component, the disposable component comprising an exterior surface and an interior surface with an adhesive coating, a first electrode part, a second electrode part, a first aperture and a second aperture, the optical sensor extending through the first aperture, the acoustic sensor extending through the second aperture, the first electrode part removably connected to the first receptor of the main component and the second electrode party removably connected to the second receptor of the main component;

a processing component for generating a blood pressure value for the user based on an electrical-based signal generated from the first electrode part and the second electrode part, an optical-based signal generated from the optical sensor, and an acoustic-based signal from the acoustic sensor; and means for transmitting information between the processing component and the monitoring component.

2. A two-component monitoring device comprising:

a disposable component comprising:
- i) a backing structure having a first aperture and a second aperture,
- ii) a first electrode and a second electrode, each of the first and second electrodes disposed on the backing structure and comprising an electrical lead in contact with a conductive electrode material, the first electrode configured to generate a first signal from the patient that passes through the conductive electrode material and the electrical lead of the first electrode, and the second electrode configured to generate a second signal from the patient that passes through the conductive electrode material and the electrical lead of the second electrode and a sensor component comprising

- i) a first connector and second connector, the first connector configured to removably connect to the first electrode to receive the first signal and the second connector configured to removably connect to the second electrode to receive the second signal,
- ii) an optical component comprising a light source that generates optical radiation and a photodetector that detects the optical radiation and generates a third signal, the optical component configured to insert through the first aperture of the backing structure, and,
- iii) an acoustic sensor configured to insert through the second aperture of the backing structure and to generate a fourth signal.

3. A two-component sensor comprising:

A disposable component configured to attach to a patient and comprising:
- i) a backing structure;
- ii) an electrode disposed on the backing structure and comprising an electrical lead in contact with a conductive electrode material, the electrode configure configured to generate a first signal from the patient that passes through the conductive electrode material and the electrical lead of the electrode; and a sensor component configured to removably connect to the disposable component and comprising:
- i) a connector configured to receive the first signal from the electrode,
- ii) an optical component comprising a light source that generates optical radiation and a photodetector that detects the optical radiation and generates a second signal, and,
- iii) an acoustic component comprising an acoustic sensor that receives an acoustic signal and generates a third signal.

* * * * *